(12) United States Patent
Kim et al.

(10) Patent No.: US 9,757,474 B2
(45) Date of Patent: Sep. 12, 2017

(54) ANTICANCER AGENT DELIVERY SYSTEM USING PH-SENSITIVE METAL NANOPARTICLES

(75) Inventors: Sungjee Kim, Gyungbuk (KR); Jutaek Nam, Gyungbuk (KR)

(73) Assignee: Postech Academy-Industry Foundation, Gyungbuk (KR)

(*) Notice: Subject to any disclaimer, the term of this patent is extended or adjusted under 35 U.S.C. 154(b) by 565 days.

(21) Appl. No.: 13/640,605

(22) PCT Filed: Apr. 7, 2011

(86) PCT No.: PCT/KR2011/002461
§ 371 (c)(1),
(2), (4) Date: Nov. 5, 2012

(87) PCT Pub. No.: WO2011/129549
PCT Pub. Date: Oct. 20, 2011

(65) Prior Publication Data
US 2013/0138032 A1   May 30, 2013
US 2013/0331764 A9   Dec. 12, 2013

(30) Foreign Application Priority Data

Apr. 15, 2010 (KR) .................. 10-2010-0034880

(51) Int. Cl.
| | | |
|---|---|---|
| *A61K 9/14* | (2006.01) | |
| *A61K 9/16* | (2006.01) | |
| *A61K 9/51* | (2006.01) | |
| *A61K 47/48* | (2006.01) | |
| *A61K 9/00* | (2006.01) | |
| *A61K 9/50* | (2006.01) | |
| *A61K 31/122* | (2006.01) | |
| *A61K 31/351* | (2006.01) | |
| *A61K 41/00* | (2006.01) | |
| *A61N 5/06* | (2006.01) | |
| *B82Y 5/00* | (2011.01) | |

(52) U.S. Cl.
CPC ...... *A61K 47/48861* (2013.01); *A61K 9/0019* (2013.01); *A61K 9/5094* (2013.01); *A61K 9/5115* (2013.01); *A61K 31/122* (2013.01); *A61K 31/351* (2013.01); *A61K 41/0052* (2013.01); *A61N 5/062* (2013.01); *B82Y 5/00* (2013.01); *Y10S 977/773* (2013.01); *Y10S 977/906* (2013.01); *Y10T 428/2982* (2015.01)

(58) Field of Classification Search
CPC ............... A61K 31/122; A61K 31/351; A61K 41/0052; A61K 47/48861; A61K 9/0019; A61K 9/5094; A61K 9/5115; A61N 5/062; B82Y 5/00; Y10S 977/773; Y10S 977/906; Y10T 428/2982
See application file for complete search history.

(56) References Cited

U.S. PATENT DOCUMENTS

| | | |
|---|---|---|
| 2002/0091242 A1 | 7/2002 | Bessodes et al. |
| 2005/0186263 A1 | 8/2005 | Bae et al. |
| 2009/0324494 A1 | 12/2009 | Ham et al. |
| 2011/0269170 A1* | 11/2011 | Kim et al. ............. 435/29 |
| 2013/0004523 A1* | 1/2013 | Zubarev et al. ......... 424/178.1 |

FOREIGN PATENT DOCUMENTS

| | | |
|---|---|---|
| KR | 2007-0042944 | 4/2007 |
| KR | 1020070042944 | 4/2007 |
| KR | 2010-0005589 | 1/2010 |
| WO | 2008/045804 A9 | 4/2008 |
| WO | WO 2010002217 A2 * | 1/2010 |

OTHER PUBLICATIONS

Prabaharan et al. Gold nanoparticles with a monolayer of doxorubicin-conjugated amphiphilic block copolymer for tumor-targeted drug delivery. Biomaterials 2009, 30:6065-6075.*
Aryal et al. Doxorubicin conjugated gold nanoparticles as water-soluble and pH-responsive anticancer drug nanocarriers. J. Mater. Chem., 2009, 19, 7879-7884.*
Prabaharan et al. Gold nanoparticles with a monolayer of doxorubicin-conjugated amphiphilic block copolymer for tumor-targeted drug delivery. Biomaterials 30 (2009) 6065-6075.*
Nam et al., J. Am. Chem. Soc. 2009, 131, 13639-13645.*
PCT, International Search Report, PCT/KR2011/002461 (mailed Dec. 14, 2011), 5 pages.
Shim & Gupta, "Reversible aggregation of gold nanoparticles induced by pH dependent conformational transitions of a self-assembled polypeptide," Journal of Colloid and Interface Science 316 (2007) 977-983.
Prabaharan et al., "Gold nanoparticles with a monolayer of doxorubicin-conjugated amphiphilic block copolymer for tumor-targeted drug delivery," Biomaterials 30 (2009) 6065-6075.
Yun et al., "Nanometal Surface Energy Transfer in Optical Rulers, Breaking the FRET Barrier," J. Am. Chem. Soc. 2005, 127, 3115-3119.
Kumar et al., "Modeling of Formation of Gold Nanoparticles by Citrate Method," Ind. Eng. Chem. Res. (2007) 46, pp. 3128-3136.

* cited by examiner

*Primary Examiner* — Robert A Wax
*Assistant Examiner* — Olga V Tcherkasskaya
(74) *Attorney, Agent, or Firm* — Baker & Hostetler LLP

(57) ABSTRACT

The present invention relates to a method for effectively delivering an anticancer drug into cancer cells by binding the anticancer drug to pH-sensitive metal nanoparticles so as to be separated from cancer cells. The pH-sensitive metal nanoparticles according to the present invention may be heated by photothermal therapy, thereby effectively killing cancer cells in conjunction with the isolated anticancer drug.

13 Claims, 6 Drawing Sheets

[FIG. 1]
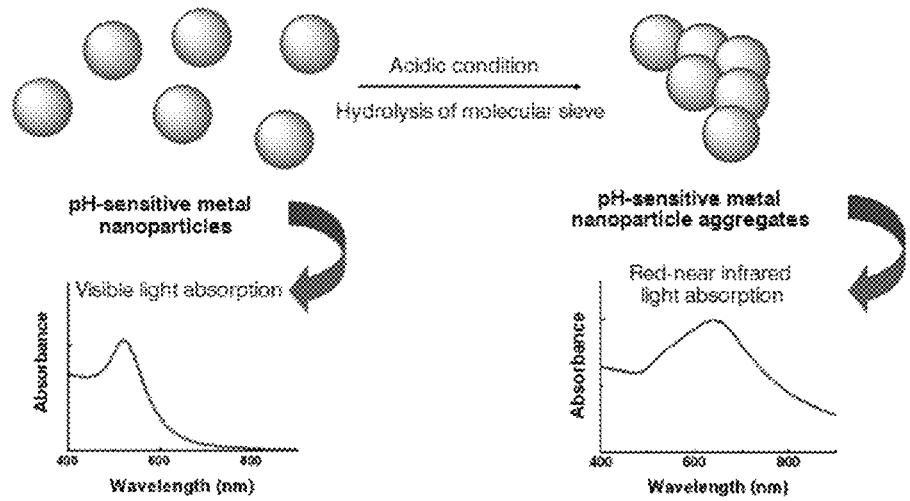
[FIG. 2]
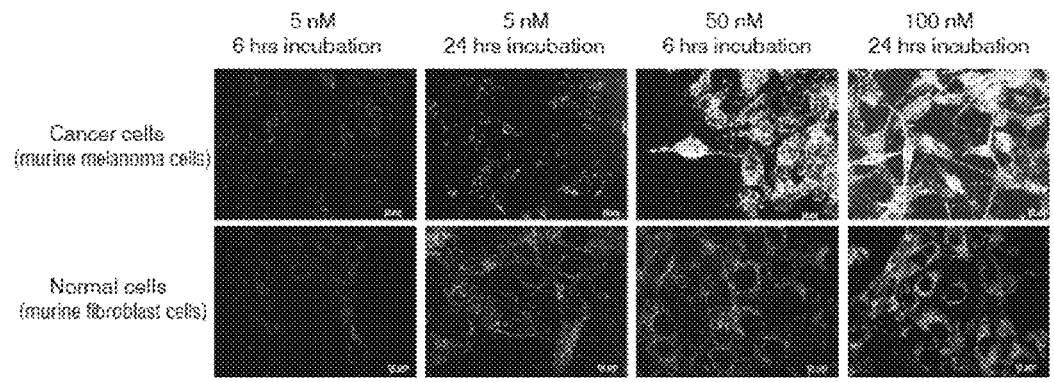

[FIG. 3]
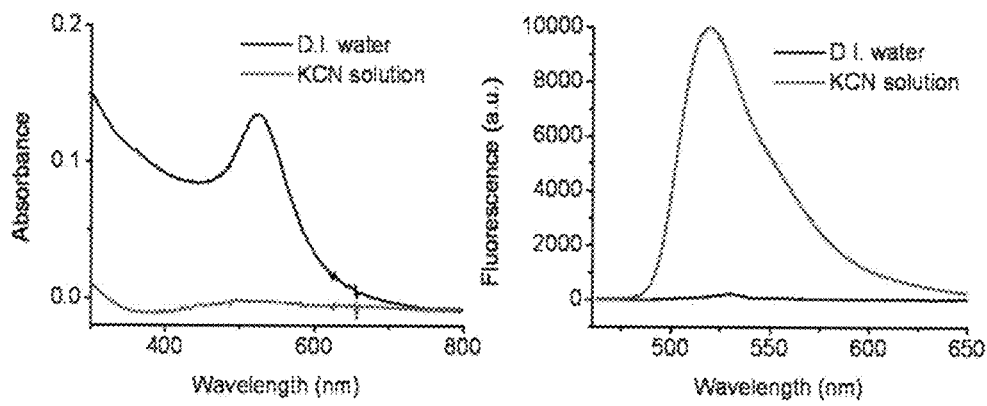
[FIG. 4]
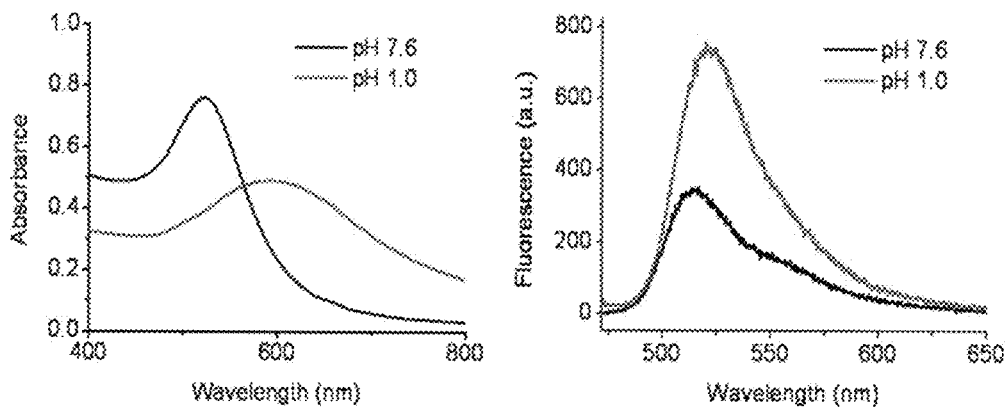

[FIG. 5]
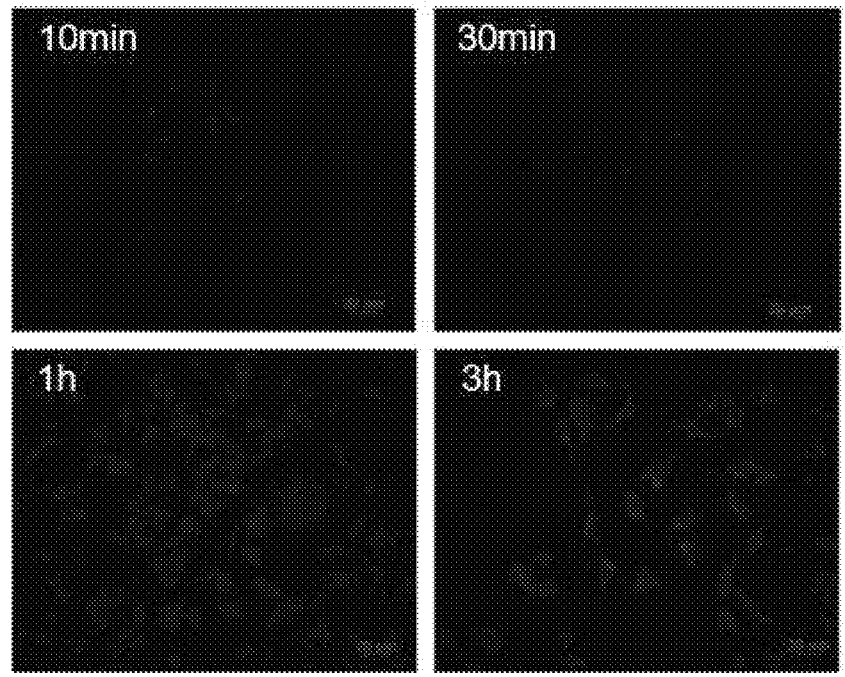

[FIG. 6]
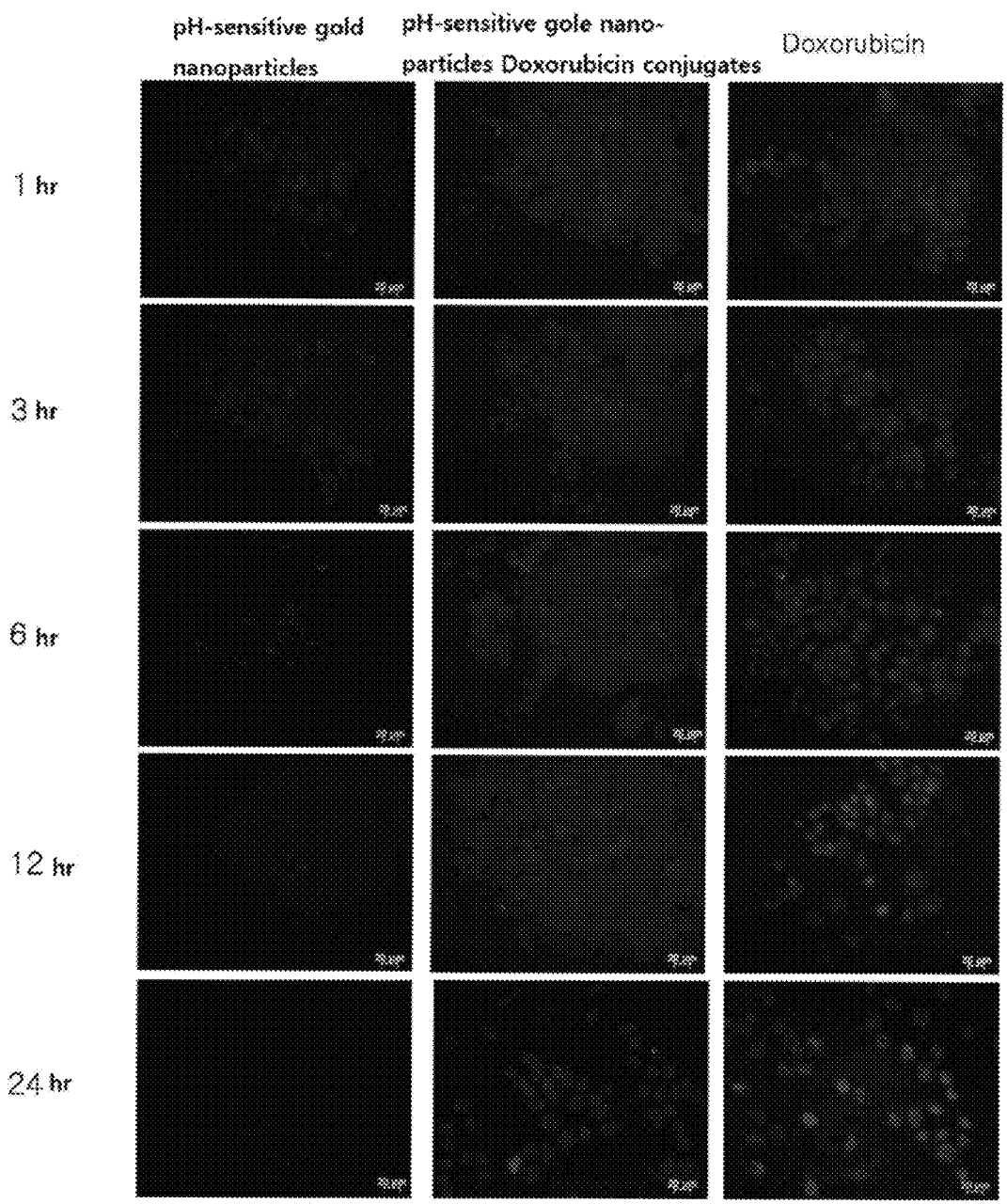

[FIG. 7]
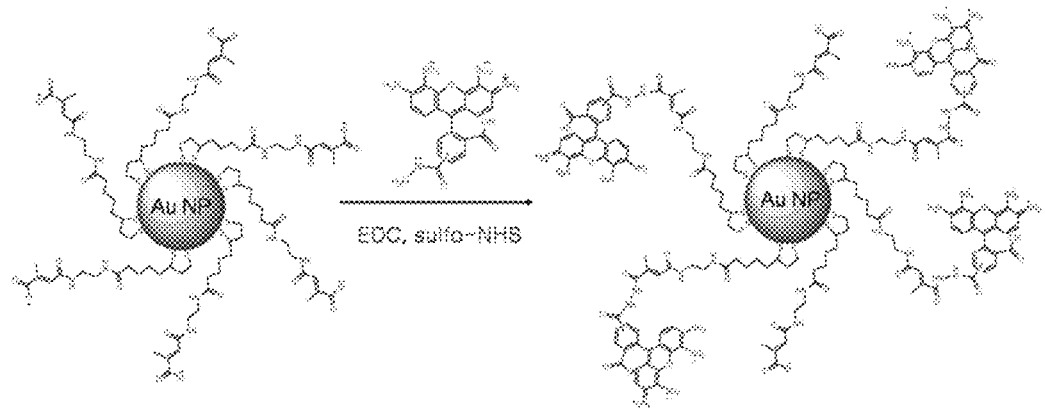
[FIG. 8]
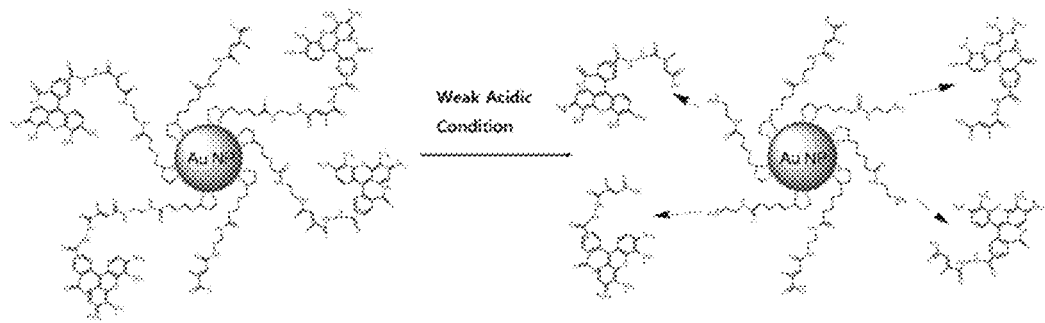
[FIG. 9]
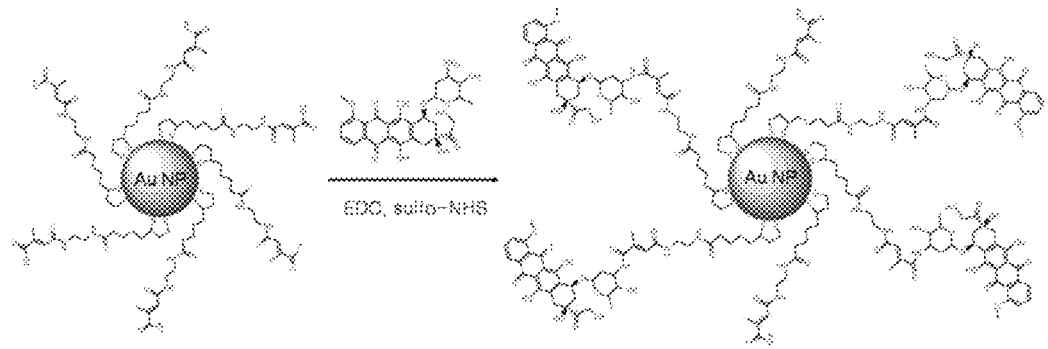

[FIG. 10]
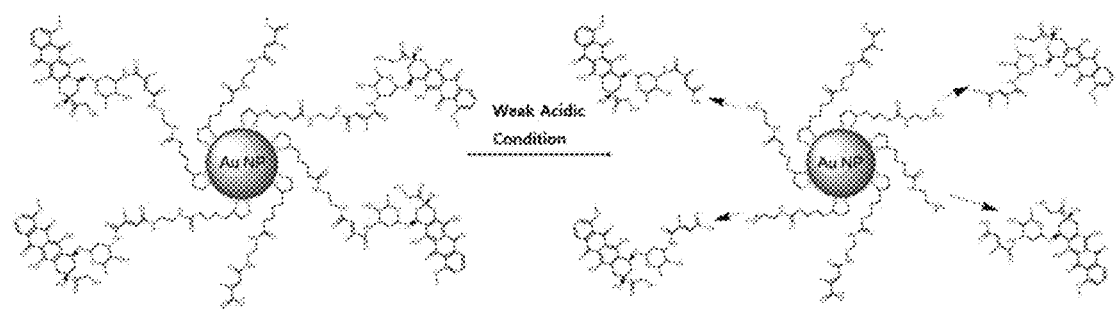

ANTICANCER AGENT DELIVERY SYSTEM USING PH-SENSITIVE METAL NANOPARTICLES

TECHNICAL FIELD

The present invention relates to a method for the delivery of anticancer agents using pH-sensitive nanoparticles, and an anticancer agent delivery system using the same.

BACKGROUND ART

Korean patent application No. 2008-0064270 teaches pH-sensitive metal nanoparticles and a preparation method thereof. These pH-sensitive nanoparticles are negatively charged and well dispersed under neutral or basic conditions. In contrast, when they are exposed to an acidic condition, their surface charges change positively as hydrolysis occurs. In this course, the nanoparticles aggregate, with their absorption band shifting from around 500 nm to greater than 600 nm, i.e., a red to near infrared region.

After entering the body, these pH-sensitive metal nanoparticles are dispersed in normal cells, which are neutral or alkaline, and selectively aggregate in cancer cells which have acidic pH. When irradiated onto the body, near infrared light with a wavelength of greater than 600 nm, which can deeply penetrate into the body, heats metal aggregates, thereby killing the cancer cells.

The pH-sensitive metal nanoparticles are selective for cancer cells and allow photothermal therapy, but by themselves have no therapeutic functions. Therefore, there is a need for new particles that can selectively aggregate in cancer cells and therapeutically treat cancer cells by themselves.

DISCLOSURE

Technical Problem

It is an object of the present invention to provide metal nanoparticles for the therapy of cancer.

It is another object of the present invention to provide novel pH-sensitive metal nanoparticles which are selective for cancer cells and can kill cancer cells by themselves.

It is a further object of the present invention to provide novel pH-sensitive metal nanoparticles which can aggregate in and release an anticancer agent to kill cancer cells.

It is still a further object of the present invention to provide a novel delivery system capable of selectively delivering an anticancer agent to cancer cells.

It is still another object of the present invention to provide the use of pH-sensitive metal nanoparticles as an anticancer agent delivery system.

It is yet a further object of the present invention to provide a method for treating cancer using particles with selectivity for and inhibitory activity against cancer cells.

Technical Solution

In accordance with an aspect thereof, the present invention provides pH-sensitive metal nanoparticles loaded with an anticancer agent, said anticancer agent being released from the nanoparticles at acidic pH.

In the present invention, "pH-sensitive metal nanoparticles" means metal nanoparticles which are dispersed under neutral or basic conditions and form aggregations at acidic pH.

Without restriction to a theory, the metal nanoparticles according to the present invention can detect and aggregate at the low pH typical of abnormal cells, such as cancer cells, functioning to treat the cancer cells with the loaded anticancer agent and to cause cell death through a photothermal process when they receive light from a light source outside of cells.

In the present invention, the metal nanoparticle is preferably small enough to penetrate into abnormal cells. In one preferred embodiment of the present invention, the metal nanoparticle is less than 20 nm in diameter and more preferably ranges in diameter from 5 to 15 nm.

According to the present invention, when the metal nanoparticles access and/or penetrate into abnormal cells, they aggregate in the cells presenting the acidic pH environment. Thereupon, the aggregated metal nanoparticles are confined within the cells and thus can be used to destroy the cells by releasing the loaded anticancer agent and allowing photothermal therapy.

When the pH environment of the metal nanoparticles is changed from alkaline to acidic, at least a portion of the compounds loaded onto the metal nanoparticles is hydrolyzed to generate a different charge from that which they have under an alkaline environment. During the charge change, the particles aggregate to each other due to electrostatic attraction. In addition, the hydrolysis separates the loaded anticancer agent from the metal particles.

In one embodiment of the present invention, the pH-sensitive metal nanoparticles may be linked with an anticancer agent through a dehydration reaction. To quote an example, an anticancer agent is loaded onto the pH-sensitive nanoparticles by a reaction between a carboxyl group and a primary amine group or between a carboxyl group and a hydroxyl group. The separation of the anticancer agent from the pH-sensitive metal nanoparticles can be achieved by hydrolysis. Preferably, the anticancer agent is released from the pH-sensitive metal nanoparticles by cleaving a different bond from the linkage bond.

In accordance with one preferable embodiment of the present invention, the metal nanoparticles have a compound represented by the following Chemical Formula 1 bound onto the surface thereof, with an anticancer agent being loaded through bond formation between the terminal carboxyl group of the compound and an amine group of the antibody drug:

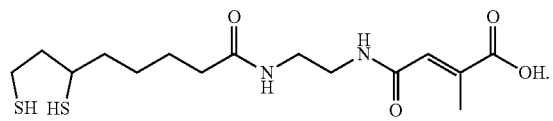

(1)

The metal nanoparticles aggregate with the concomitant release of the anticancer agent therefrom as the compound of Chemical Formula 1 undergoes hydrolysis at acidic pH and thus changes in charge. The hydrolysis which causes the compound of Chemical Formula 1 to change in charge is described in Korean patent application No. 2008-0064270, the disclosure of which is herein incorporated by reference in its entirety.

In one embodiment of the present invention, the anticancer agent is released with the $NH_2$ group being substituted with the moiety represented by the following Chemical Formula 2:

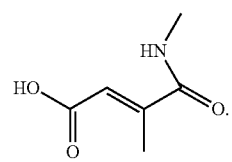

(2)

According to one embodiment of the present invention, the anticancer agent may be a well-known therapeutic drug for cancer, such as Methotrexate, Paclitaxel, Cisplatin, Bleomycin and the like.

In another embodiment of the present invention, as long as it is loaded to the metal nanoparticles, any anticancer agent may be used in the present invention. Examples of the anticancer agent useful in the present invention include photosensitizers for photodynamic therapy, such as aminolevulinic acid, Temoporfin, etc., amine- or hydroxy-modified genetic therapeutics such as siRNA, antisense oligonucleotides, ribozymes, etc., aptamers, and protein-based therapeutics such as antibodies and the like, as well as chemical drugs that directly attack cancer cells.

In accordance with another aspect thereof, the present invention addresses a therapeutic for cancer, comprising a metal nanoparticle onto which a molecule of Chemical Formula 1 is anchored, with an anticancer agent being conjugated to the molecule at one terminus:

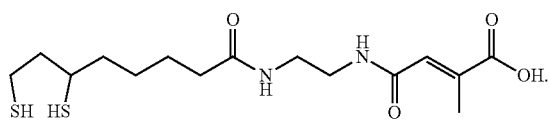

(1)

Without restriction to a theory, the anticancer agent conjugated to the surface molecule of Chemical Formula 1 is released from the metal nanoparticle and exerts its therapeutic effect on cancer cells as the surface molecule is hydrolyzed in a pH condition of cancer cells.

In accordance with a further aspect thereof, the present invention addresses a method for delivering an anticancer agent into cancer cells using metal nanoparticles loaded with the anticancer agent which selectively aggregates in cancer cells. The anticancer agent loaded onto the nanoparticles is released from the nanoparticles to exert an anticancer effect on cancer cells.

In accordance with still a further aspect thereof, the present invention pertains to a method for treating cancer, comprising administering pH-sensitive metal nanoparticles loaded with an anticancer agent to a subject in need thereof, said pH-sensitive metal nanoparticles aggregating in abnormal cells, and irradiating the aggregated pH-sensitive metal nanoparticles with light to conduct a photothermal therapy.

Also, contemplated in accordance with still another aspect of the present invention is to provide pH-sensitive metal nanoparticles the surface of which is conjugated with a fluorescent dye.

In one embodiment of the present invention, the organic dye Alexa Fluor 488 hydrazide is introduced into the molecule on the surface of the pH-sensitive gold nanoparticles. The fluorescent dye Alexa Fluor 488 hydrazide emits green light with a wavelength of around 520 nm.

Without restriction to a theory, when a dye introduced into the surface of the metal nanoparticle is in close proximity to the metal nanoparticles with a distance of 10 nm or less therebetween, the fluorescence energy can be transferred to the surface of the metal nanoparticle. In this regard, NSET (Nanoparticle Surface Energy Transfer) appears, in which the fluorescence extinguishes as the transferred fluorescence energy on the surface is emitted through a different pathway (Yun, C. S., Javier, A., Jennings, T., Fisher, M., Hira, S., Peterson, S., Hopkins, B., Reich, N. O., and Strouse, G. F., J. Am. Chem. Soc. 2005, 127, 3115-3119). This characteristic optical property can be used to monitor the introduction of the dye to the surface of the metal nanoparticles.

In accordance with yet a further aspect thereof, the present invention addresses a metal nanoparticle conjugated with the compound of Chemical Formula 3, for use in the therapy of cancer:

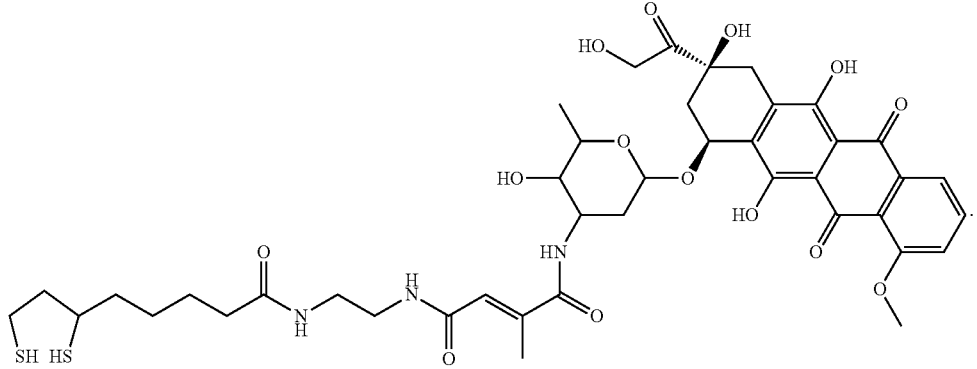

(3)

In accordance with yet another aspect thereof, the present invention provides a therapeutic compound represented by the following Chemical Formula 4:

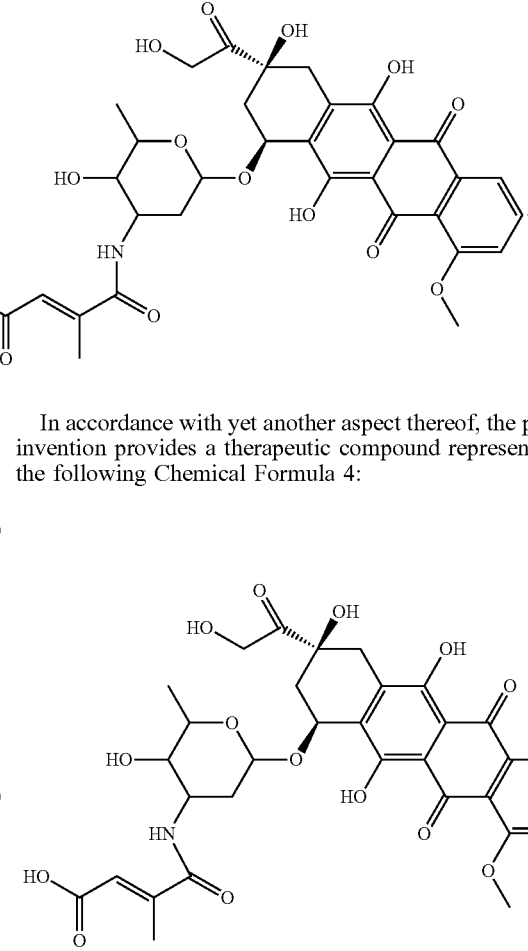

(4)

Advantageous Effects

As described above, the novel metal nanoparticles of the present invention are selective for cancer cells and can be used in the therapy of cancer. Further, because the pH-sensitive metal nanoparticles of the present invention are loaded with an anticancer drug, the cancer therapy of the present invention is a combination of photothermal therapy and chemotherapy.

In addition, when loaded with a therapeutic or diagnostic agent, the novel metal nanoparticles of the present invention can deliver the agent into cancer cells, thus establishing a novel therapeutic and diagnostic method.

Further, the pH-sensitive gold nanoparticles are selective for cancer cells, thereby allowing a selective cancer therapy with minimal damage of an anticancer agent to normal cells. Moreover, the introduction of a targeting molecule such as an antibody or an aptamer is expected to further enhance therapeutic efficacy for cancer.

Being able to exert light- and chemical-based therapeutic effects on cancer, the metal nanoparticles of the present invention takes advantage of a combination of photothermal therapy and chemotherapy, which may lead to more selective and potent ability to kill cancer cells.

BRIEF DESCRIPTION OF THE DRAWINGS

FIG. 1 is a conceptional view showing that the absorption band of pH-sensitive metal nanoparticles changes as surface molecules on the pH-sensitive gold nanoparticles are hydrolyzed.

FIG. 2 shows dark-field microphotographs of cancer cells and normal cells incubated with various concentrations of pH-sensitive metal nanoparticles for a predetermined period of time.

FIG. 3 shows absorbance (left panel) and fluorescence (right panel) spectra of a solution of pH-sensitive gold nanoparticle-Alexa Fluor 488 hydrazide conjugate (black) and a solution in which the gold nanoparticles are dissolved with KCN (red).

FIG. 4 shows absorbance (left panel) and fluorescence (right panel) spectra of dispersions of the pH-sensitive gold nanoparticle-Alexa Flour 488 hydrazide conjugates at pH 7.6 (black) and at pH 1.0 (red).

FIG. 5 shows fluorescence microphotographs of murine melanoma cells incubated with the pH-sensitive gold nanoparticle-Alexa Fluor 488 hydrazide conjugates for 1 hour (left panel in the second line) and for 3 hours (right panel in the second line).

FIG. 6 shows fluorescence microphotographs of breast cancer cells incubated with the pH-sensitive gold nanoparticle-doxorubicine conjugates for a test group (middle panels), the pH-sensitive gold nanoparticles for a negative control (left panels) and doxorubicine for a positive control (right panels). As doxorubicine is delivered into cells, the nuclei appear yellow-reddish due to the fluorescence of doxorubicine. Incubation hours are indicated on left sides of columns.

FIGS. 7 to 10 are schematic views illustrating the formation of conjugates with surface molecules of pH-sensitive gold nanoparticles.

MODE FOR INVENTION

Examples

Synthesis of pH-Sensitive Ligand

A solution of lipoic acid in anhydrous chloroform was mixed at room temperature for 5 min with 1.3 equivalents of carbonyl diimidazole under a vacuum condition with stirring, followed by separating the reaction solution layer from the remaining carbonyl diimidazole. Ethylene diamine was dissolved in an amount corresponding to 5 equivalents of the lipoic acid in anhydrous chloroform in a nitrogen atmosphere, cooled in an ice bath, and mixed for 1 hour with the separated reaction solution by stirring. The resulting reaction solution containing the product was extracted three times with 10% NaCl and once with deionized water and mixed at room temperature for 24 hours with citraconic anhydride to form a solid substance. After filtration, the solid substance was dissolved in an aqueous solution which was adjusted to a pH of 9 with NaOH. The resulting solution was stirred at room temperature for 4 hours together with one equivalent of $NaBH_4$ to afford a pH-sensitive ligand.

Synthesis of Gold Nanoparticles Stabilized with Citrate

A solution of the gold precursor $HAuCl_4$ in distilled water was heated at 120° C. for 30 min with stirring, and then for an additional 2 h, together with trisodium citrate, with stirring. In this course, the trisodium citrate acted as a reducing agent and a surface ligand, with the solution turning from yellow to red, indicating the construction of gold nanoparticles. Thereafter, the solution was cooled at room temperature with stirring. (*Ind. Chem. Res.* 2007, 46, 3128-3136)

Synthesis of pH-Sensitive Gold Nanoparticles

The citrate-stabilized gold nanoparticles were added to an aqueous solution containing an excess of the synthetic pH-sensitive ligand and mixed at room temperature for 8 hours by stirring. Because the dithiol of the pH-sensitive ligand binds more strongly to the surface of the gold nanoparticles than does the carboxylic acid of citrate, the pH-sensitive ligand is exchanged for the citrate. Excess ligands were removed by dialysis.

Conjugation of pH-Sensitive Gold Nanoparticle with Drug

1) Synthesis of pH-Sensitive Gold Nanoparticle-Alexa Fluor 488 Hydrazide Conjugate A dispersion of pH-sensitive gold nanoparticles in a phosphate buffer, pH 7.0, was stirred, together with excess 1-ethyl-3-(3-dimethylaminopropyl)carbodiimide (EDC) and sulfo-N-hydroxy succinimide (sulfo-NHS), at room temperature for 10 min to activate the pH-sensitive gold nanoparticles. The solution was dialyzed three times against a phosphate buffer, pH 7, to remove excess EDC and sulfo-NHS. The dialyzed solution was mixed at room temperature for 3 hours with a dispersion of Alexa Fluor 488 hydrazide in distilled water with stirring, so as to form a pH-sensitive gold nanoparticle-Alexa Fluor 488 hydrazide conjugate. Excess Alexa Fluor 488 hydrazide was removed by three rounds of dialysis with distilled water.

In the context of the conjugation, EDC and sulfo-NHS, both for use in the conjugation, acted as molecules to promote the formation of an amide bond between the terminal carboxylic acid of the pH-sensitive gold nanoparticles and the primary amine group of Alexa Fluor 488 hydrazide, as illustrated in FIG. 7.

Upon exposure of the conjugate to a weak acidic condition such as an environment presented by endosomes within cells, the surface molecules on the pH-sensitive gold nanoparticles undergo hydrolysis so that the Alexa Fluoro 488 hydrazide is released from the gold nanoparticles, as illustrated in FIG. 8.

2) Synthesis of pH-Sensitive Gold Nanoparticle-Doxorubicin Conjugate

Excess 1-ethyl-3-(3-dimethylaminopropyl)carbodiimide (EDC) and sulfo-N-hydroxy succinimide (sulfo-NHS) were added to a dispersion of pH-sensitive gold nanoparticles in a phosphate buffer, pH 7.0, and stirred at room temperature for 10 min to activate the pH-sensitive gold nanoparticles. The solution was dialyzed three times against a phosphate buffer, pH 7, to remove excess EDC and sulfo-NHS. The dialyzed solution was mixed at room temperature for 3 hours with a dispersion of doxorubicin in a phosphate buffer, pH 8.0, with stirring, so as to form a pH-sensitive gold nanoparticle-doxorubicin conjugate.

The pH-sensitive gold nanoparticle-doxorubicin conjugate was used, without further purification, for culturing cells. In the context of the conjugation, EDC and sulfo-NHS, both for use in the conjugation, acted as molecules to promote the formation of an amide bond between the terminal carboxylic acid of the pH-sensitive gold nanoparticles and the primary amine group of doxorubicin, as illustrated in FIG. 9.

When the pH-sensitive gold nanoparticles encounter endosomes presenting a weak acidic environment, the surface molecules on the pH-sensitive gold nanoparticles are hydrolyzed to release the doxorubicin from the gold nanoparticles.

Concurrently, the surface charge of the pH-sensitive gold nanoparticles changes from (−) to (+) so that the particles aggregate due to electrostatic attraction. As the pH-sensitive gold nanoparticles aggregate, their light absorption band shifts toward longer wavelengths. Therefore, the pH-sensitive gold nanoparticles of the present invention allow for photothermal therapy with long wavelength light as well as for chemotherapy through the delivery of an anticancer drug to cancer cells.

Fluorescence Assay

KCN was added to a solution of pH-sensitive gold nanoparticle-Alexa Fluor 488 hydrazide conjugate to dissolve the gold. This gold-dissolved solution and a solution of pH-sensitive gold nanoparticle-Alexa Fluor 488 hydrazide conjugate were examined for light absorption and fluorescence properties.

As can be seen in the absorbance spectra of FIG. 3, the conjugate solution had an absorption band at around 500 nm, which is typical of a dispersion of gold nanoparticles, indicating that the gold nanoparticles were well and stably dispersed even after conjugation with the dye (left panel, black).

Upon the treatment of the gold nanoparticles with KCN, the characteristic absorbance of gold nanoparticles disappeared, indicating that the gold nanoparticles were completely dissolved (left panel, red).

Turning to fluorescence spectra (FIG. 3, right panel), fluorescence intensity was detected at a very low level in the conjugate solution, but was increased 50-fold after the solubilization of the gold nanoparticles with KCN.

The fluorescence spectra describe the extinguishment of dye fluorescence by gold nanoparticles, demonstrating that the pH-sensitive gold nanoparticles were successfully loaded with dye to form a stable conjugate.

When the conjugate in which a molecule of interest is introduced into the terminal of the surface molecules anchored onto the surface of the pH-sensitive gold nanoparticle is exposed to a weak acidic condition, the terminal functional group is cleaved by hydrolysis to release the molecule of interest, with the concomitant formation of aggregates of nearby particles by electrostatic attraction.

To confirm this, the pH-sensitive gold nanoparticle-Alexa Fluor 488 hydrazide conjugates were dispersed at pH 7.6 and pH 1.0, and absorbance and fluorescence spectra were measured.

As shown in the absorbance spectra of FIG. 4 (left), the conjugates were well dispersed at pH 7.6, having an absorbance band of around 500 nm, whereas at pH 1.0, they rapidly aggregated, with the absorbance band shifting to a wavelength of 600 nm or longer.

As can be seen in the fluorescence spectra of FIG. 4 (right), the fluorescence intensity of Alexa Fluor 488 hydrazide was increased at pH 1.0, compared to pH 7.6, indicating that when exposed to an acidic condition, the gold nanoparticle function of extinguishing the fluorescence of Alexa Fluor 488 hydrazide was lost and that the Alexa Fluor 488 hydrazide introduced into the surface of the pH-sensitive gold nanoparticles was dissociated from the surface and became more distant from the gold nanoparticles.

Taken together, the data obtained above demonstrate that the pH-sensitive nanoparticle-Alexa Fluor 488 hydrazide conjugates release the Alexa Fluor 488 hydrazide moiety in an acidic condition while the gold nanoparticles aggregate with the absorbance band shifting toward longer wavelengths.

FIG. 5 shows fluorescence photographs of murine melanoma cells incubated with pH-sensitive gold nanoparticle-Alexa Fluor 488 hydrazide conjugates, illustrating that the fluorescence intensity of the Alexa Fluor 488 hydrazide increases with time within cells.

Once the conjugates are internalized into cells, the conjugates undergo hydrolysis, when encountering an intracellular acidic pH environment such as endosomes, to induce the dissociation of the Alexa Fluor 488 hydrazide moiety. Thereupon, the fluorescence of Alexa Fluor 488 hydrazide which has been extinguished by energy transfer into the gold nanoparticles revives, so that green fluorescence is visualized within cells under a fluorescence microscope.

Fluorescence was observed at a very small intensity in the cells 10 to 30 min after incubation with the conjugate, but started to intensify from one hour after the incubation and reached the maximum three hours after the incubation.

This result shows that after the internalization of the pH-sensitive gold nanoparticles into cells, Alexa Fluor 488 hydrazide is released gradually.

Taking advantage of the phenomenon that after internalization into cells, the pH-sensitive gold nanoparticle conjugates undergo hydrolysis to gradually dissociate the conjugated molecule with time, the pH-sensitive gold nanoparticles of the present invention can be used as a drug delivery system.

Drug Test

In this Example, the anticancer drug doxorubicin was employed. Doxorubicin works to induce cell death by intercalating DNA. It emits yellow-reddish fluorescence at near 600 nm. When the conjugates penetrate into cancer cells, doxorubicin is dissociated from the gold nanoparticles by hydrolysis under an acidic condition and translocates into the nucleus which thus emits yellow-reddish fluorescence. Test results are shown in FIG. 6.

Breast cancer cells in test groups were incubated with the pH-sensitive gold nanoparticle-doxorubicin conjugates to induce the internalization of the conjugate (middle panel, FIG. 6).

For comparison, cells were incubated with doxorubicin-free pH-sensitive gold nanoparticles (left panel, FIG. 6) and with doxorubicin alone (right panel, FIG. 6) under the same condition.

The intranuclear delivery of doxorubicin can be qualitatively analyzed in terms of nuclear yellow-reddish fluorescence as measured by fluorescence microscopy.

Because of the absence of doxorubicin, the cells treated with the pH-sensitive gold nanoparticles alone did not show fluorescence in the nucleus 24 hours after incubation.

In contrast, the fluorescence of doxorubicin started to appear with time in the cells treated with the pH-sensitive gold nanoparticle-doxorubicin conjugates. The nuclei were observed to be clearly fluorescent 12 hours after incubation ($4^{th}$ column, middle panel, FIG. 6). Further intense fluorescence was detected 24 hours after incubation ($5^{th}$ column, middle panel, FIG. 6).

On the other hand, the cells incubated with doxorubicin alone started to exhibit fluorescence after only one hour of incubation ($1^{st}$ column, right panel, FIG. 6) and the fluorescence was intensified after 3 hours of incubation ($3^{rd}$ column, right panel, FIG. 6). Thereafter, the fluorescence intensity increased with time, but relatively insignificantly.

While intense fluorescence is detected within a short culture time upon treatment with doxorubicin alone, the fluorescence intensity of pH-sensitive gold nanoparticle-doxorubicin conjugates is relatively slowly increased.

However, similar fluorescence intensities were obtained after 24 hours in both cell groups, indicating that levels of doxorubicin delivered into the nucleus become similar after a sufficient period of time. That is, most of the doxorubicin conjugated to the pH-sensitive gold nanoparticles is released.

In order for doxorubicin to be visualized in the cells incubated with the pH-sensitive gold nanoparticle-doxorubicin conjugates, the conjugates must be internalized into the cells and hydrolyzed to dissociate the doxorubicin therefrom.

Hence, a series of processes of internalizing the pH-sensitive metal nanoparticle-doxorubicin conjugates into cells and hydrolyzing the conjugates at acidic endosomes to release doxorubicin is conducted relatively slowly so that it takes relatively much time for doxorubicin to accumulate in the nucleus of cells.

Based on the data, the pH-sensitive metal nanoparticles on which a surface molecule is conjugated with an anticancer drug can be used as an anticancer drug delivery system which allows drug release to be easily controlled, compared to the drug alone.

When administered into the body, anticancer drugs alone can accumulate in the nuclei of cells within a short period of time, thus exerting pharmaceutical effects like the administration of an excessive amount of drug. In contrast, conjugates with the pH-sensitive metal nanoparticles release the drug for a relatively long period of time, showing pharmaceutical effects like sustained-release type of drugs.

In this way, if drug release is controlled through the conjugate system of the pH-sensitive metal nanoparticles, not only can the adverse effects related to overdose or insufficient dose of drug be reduced, but also the inconvenience of patients attributed to frequent administration can be alleviated. In addition, the pH-sensitive gold nanoparticles enjoy the advantage of improving the poor solubility of anticancer drugs thanks to their high solubility and recruiting a variety of anticancer drugs.

Gene therapeutics such as siRNA as well as conventional anticancer agents such as doxorubicin can be used in the present invention.

In addition to the delivery of anticancer drugs, the pH-sensitive metal nanoparticles function to perform potent photothermal therapy as they aggregate after releasing the anticancer drugs for chemotherapy. Therefore, the pH-sensitive metal nanoparticles are advantageous in that they can more effectively kill cancer cells through a combination of chemotherapy and photothermal therapy.

With these advantages, the pH-sensitive metal nanoparticle-anticancer drug conjugate is expected to be an effective anticancer drug delivery system.

The invention claimed is:

1. pH-sensitive metal nanoparticles for therapy of cancer, being loaded with an anticancer drug through a linkage bond, wherein the anticancer drug is released from the metal nanoparticles in an acidic pH condition to kill a cancel cell, and the metal nanoparticles form aggregations in an acidic pH condition for photothermal therapy so as to kill the cancer cell by absorbing red or near-infrared light, and wherein the anticancer drug is released from the pH-sensitive nanoparticles by cleaving a different bond than the linkage bond.

2. The pH-sensitive metal nanoparticles of claim 1, having a compound anchored onto a surface thereof, said compound being represented by the following Chemical Formula 1:

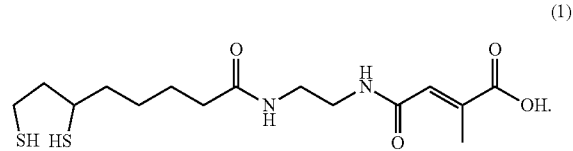 [SMILES: C/C(=C\C(=O)NCCNC(=O)CCCCC(S)CCS)C(=O)O]

3. The pH-sensitive metal nanoparticles of claim 1, ranging in size from about 5 nm to 15 nm.

4. The pH-sensitive metal nanoparticles of claim 1, wherein the anticancer drug is released by hydrolysis.

5. The pH-sensitive metal nanoparticles of claim 1, wherein the anticancer drug is selected from the group consisting of doxorubicin, Methotrexate, Paclitaxel, Cisplatin, Bleomycin, and a combination thereof.

6. The pH-sensitive metal nanoparticles of claim 2, wherein the anticancer drug has a —$NH_2$ group, said —$NH_2$ group being substituted by a compound represented by the following Chemical Formula 2, when releasing:

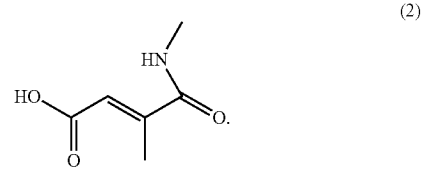

7. A metal nanoparticle being conjugated with a compound represented by the following Chemical Formula 3:

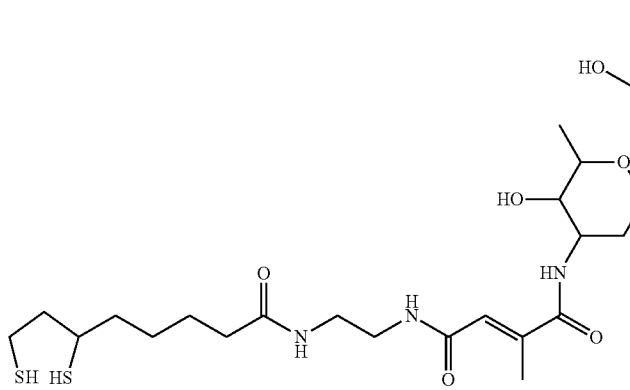

(3)

8. A compound represented by the following Chemical Formula 4:

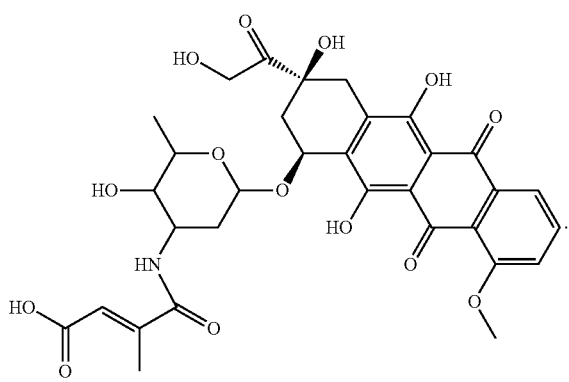

(4)

9. A pH-sensitive metal nanoparticle having a compound anchored onto a surface thereof, said compound represented by the following Chemical Formula 1, being conjugated with a dye having a primary amine group or an —OH group:

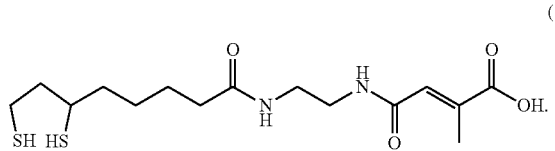

(1)

10. The pH-sensitive metal nanoparticle of claim 9, wherein the dye is Alexa Fluor 488 hydrazide.

11. A pH-sensitive metal nanoparticle, being conjugated with an agent having a primary amine group or a —OH group, said agent being selected from the group consisting of an anticancer agent, a light sensitizer, a gene therapeutic, a protein therapeutic, and a combination thereof.

12. An anticancer agent having one or more —NH$_2$ groups, wherein at least one —NH$_2$ group is substituted by a compound represented by the following Chemical Formula 2:

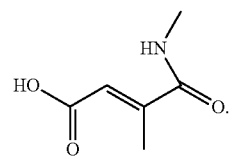

(2)

13. The pH-sensitive metal nanoparticles of claim 1, wherein the anticancer agent is covalently linked by a reaction between a —COOH group of the linkage compound and an —NH2 group of the anticancer agent, and released from the metal nanoparticles by cleaving a different bond from the linkage bond.

* * * * *